(12) United States Patent
Latorre Rojas et al.

(10) Patent No.: US 12,102,761 B2
(45) Date of Patent: Oct. 1, 2024

(54) NASAL OXYGEN CANNULA WITH DEVICE FOR MEASURING USE TIME

(71) Applicant: FUNDACION ABOOD SHAIO EN REESTRUCTURACION, Bogota (CO)

(72) Inventors: Carlos Javier Latorre Rojas, Bogota (CO); Maria Lucia Arango Cortes, Bogota (CO); Fabian Cortes Munoz, Bogota (CO); Jenny Carolina Sanchez Casas, Bogota (CO)

(73) Assignee: FUNDACION ABOOD SHAIO EN REESTRUCTURACION, Bogota (CO)

( * ) Notice: Subject to any disclaimer, the term of this patent is extended or adjusted under 35 U.S.C. 154(b) by 773 days.

(21) Appl. No.: 17/416,641

(22) PCT Filed: Jul. 17, 2019

(86) PCT No.: PCT/IB2019/056103
§ 371 (c)(1),
(2) Date: Jun. 21, 2021

(87) PCT Pub. No.: WO2021/009546
PCT Pub. Date: Jan. 21, 2021

(65) Prior Publication Data
US 2022/0096771 A1    Mar. 31, 2022

(51) Int. Cl.
*A61M 16/06* (2006.01)
*A61M 16/00* (2006.01)
*A61M 16/20* (2006.01)

(52) U.S. Cl.
CPC .... *A61M 16/0666* (2013.01); *A61M 16/0003* (2014.02); *A61M 2205/3553* (2013.01); *A61M 2205/50* (2013.01)

(58) Field of Classification Search
CPC ....... A61M 16/0666–0677; A61M 2039/1005; A61M 15/08; A61M 15/085; A62B 23/06
See application file for complete search history.

(56) References Cited

U.S. PATENT DOCUMENTS

| 7,222,624 | B2 | 5/2007 | Rashad et al. |
| 8,631,799 | B2 | 1/2014 | Davenport et al. |
| 9,078,989 | B2 | 7/2015 | Genger et al. |
| 2018/0361099 | A1* | 12/2018 | Wells .................. A61M 15/085 |

FOREIGN PATENT DOCUMENTS

EP    1935445 A2    6/2008

* cited by examiner

*Primary Examiner* — Joseph D. Boecker
*Assistant Examiner* — Mautin I Ashimiu
(74) *Attorney, Agent, or Firm* — Patenting Consulting Group; Roberto J. Rios

(57) ABSTRACT

The present invention relates to a nasal oxygen cannula, which has a simple and economic design that reduces drug wastage and allows the effective use time to be measured in order to effectively monitor oxygen therapy treatment in patients with spontaneous breathing. Structurally, the cannula is formed by a mechanical system that is only activated when it comes into physical contact with the patient́s columella, and an electronic component that allows the real use time of the device to be measured by means of an electric actuator that triggers an electric pulse the moment the cannula is in place on the user.

8 Claims, 11 Drawing Sheets

NASAL OXYGEN CANNULA WITH DEVICE FOR MEASURING USE TIME

FIELD OF THE INVENTION

The present invention is in the field of nasal oxygen cannula technologies. More specifically, the disclosure refers to a cannula which, thanks to a simple and inexpensive internal configuration, avoids medication waste and allows the measurement of the effective time of use.

BACKGROUND OF THE INVENTION

Oxygen therapy is a technique consisting of supplying additional oxygen to that available in the environment, in pathological conditions where it is not possible to reach the concentrations required for the adequate performance of aerobic metabolic processes. Through this therapy, the continuous flow of oxygen is reestablished, thus increasing its availability in the blood.

In this therapy, the delivery time of the medication is essential to allow the restoration of normal oxygen levels in the blood. Thus, if the administration occurs for a shorter period than suggested, the desired oxygen level will probably not be recovered and, on the contrary, if the administration of oxygen exceeds the required basal concentrations, it produces alterations that trigger metabolic and respiratory pathologies.

However, monitoring the dosage of said therapy is complex since there may be shortcomings in the supply: from the source that administers the medication (medicinal oxygen system, oxygen tank, etc.) to the device that is used to supply it to the patient (cannula). For the latter in particular, there is no technology available on the market that allows monitoring continuous supply, taking into account that the patient can withdraw it due to factors such as discomfort, fatigue for use or others related to social integration, thus, the treatment becomes intermittent and is not as effective.

This means real time measurement of use of the device used to supply oxygen dosage, contributes to generating a more effective treatment and control in patients with lung disease, thus avoiding the waste of the medication and the increase in treatment costs. Currently, there are multiple strategies on the market that improve the oxygen administration equipment used in oxygen therapy, such as modifying the conventional cannula from the incorporation of sensors that allow evaluating the characteristics of the fluid and/or the use of motors to automate the system allowing even to generate positive pressures on the patient.

For example, U.S. Pat. No. 7,222,624B2 discloses a method and a nasal cannula for supplying oxygen to a patient in response to the patient's pulse rate and blood hemoglobin saturation. Said system has two non-invasive sensors that measure patient's blood hemoglobin saturation and pulse rate in order to compare these measurements with already defined limits and respond in such a way that the variables are modulated to a desired level.

Despite the obvious advantages of such automated devices, the vast majority are expensive and complex in design to achieve wide commercialization in the healthcare industry. Thus, the conventional cannula continues to be the current predominant device on the market. Therefore, there is a need in the state of the art to create conventional cannulas that incorporate simple and inexpensive improvements allowing precise control of the time of use of medication delivery in order to ensure the success of oxygen therapy.

DESCRIPTION OF THE INVENTION

Therefore, the cannula of the present invention has a simple and economical configuration that allows the control of the consumption of medical oxygen by means of a mechanical trigger and reports the effective supply of said fluid in units of time to a digital central that stores said data.

One of the advantages of the invention is that the calculation of the real time of use makes possible an estimation of the oxygen flow that is administered to the patient. The foregoing is novel because the present system takes into account only the time in which there was physical contact between the patient's columella and the oxygen cannula and, therefore, the actual supply of the medication. Thus, the system does not count the time of use of the moments in which the cannula was removed or was not properly adjusted to the patient and therefore will contribute to the assessment of the treatment effectiveness.

Another technical advantage of the cannula of the invention is based on the fact that it reduces the waste of medicinal oxygen. This is because the administration of the medication only occurs when there is physical contact between an element of the mechanical system of the cannula and the patient's columella. Thus, the administration of oxygen stops automatically when the cannula is removed from the nostrils.

The cannula of the present invention allows effective monitoring of oxygen therapy treatment in patients.

Another advantage of the cannula depicted here is that it does not modify the use of the conventional cannula or require additional steps.

Likewise, the cannula of the present invention has a simple and inexpensive design that is easy for patients to access and which does not require highly complex instructions.

The cannula disclosed herein is composed of a mechanical system that is activated only when it comes into physical contact with the patient's columella and an electronic component that allows the measurement of the device actual time of use.

The mechanical system of the invention is composed of a mechanical activator that allows the passage of oxygen only when the cannula is correctly positioned in the patient's nostrils.

For its part, the electronic component of the invention comprises an electrical actuator that is capable of triggering an electrical pulse when the user wears the cannula. From this, the system calculates the actual time of use of the cannula by means of a microprocessor.

Structurally, the cannula comprises a plastic tube (1a) with four openings: two directed to the nostrils (1a) and two (1b) connected to two hoses (4) directed to a source of medicinal oxygen.

The mechanical system of the cannula of the present invention is located between the two nostrils (1a) and is composed of a sliding folded gate (2b) joined to a retractable element (2c) installed on a base (2d); said base in turn is connected to elements (2e) that direct the movement and can be arranged in pairs in the direction of the two openings (1b), its function is to provide the gate (2b) with stability and ease of movement.

When the retractable element (2c) contracts, it displaces the gate (2b) which unfolds through the displacement directing elements (2e). When fully deployed, the holes of the gate (2b) are located parallel to the openings (1a) generating a pressure gradient that allows the circulation of oxygen.

The mechanical system (2) of the cannula is covered by an outer covering (2a) fixed to the plastic tube (1a) that comes into direct contact with the patient's columella; thus, the actuator for bending the retractable element turns out to be the patient's columella when the two openings (1a) are located in the nostrils.

Regarding the electronic component of the cannula that allows to measure the real time of use, an electronic sensing system (3) is arranged on the base (2d). Said electronic system comprises sensors (3a) that detect the deployment of the gate (2b) and send an electronic signal through transmission cables (3b), arranged in the posterior region of the cannula, to a data collection system.

The data collection system may include, as an example only, an analog-digital component that includes a power supply system for the sensors (3a), a processing system consisting of a controller, processor or microprocessor that acquires the analog data recorded by the sensors and executes processing tasks such as patient ID generation, time counter and storage, and a wireless data transmission system to a receiving device such as a computer, tablet, smartphone, among others. In this device, the data is classified by patient in order to calculate variables such as the time of oxygen consumption or the intervals of pauses taken.

The processing system can also quantify the dosage and consumption if there are variables associated with the characteristics of the dosage system such as the oxygen outlet pressure, the storage volume, the cannula size and variables associated with the patient such as height and weight.

In a preferred embodiment of the invention, the retractable element (2c) of the mechanical system can be a spring.

In another preferred embodiment, the displacement directing elements (2e) of the mechanical system may include, but are not limited to, rails or channels.

In a preferred embodiment, the number of displacement directing elements (2e) of the mechanical system is four.

In a preferred embodiment, the cover (2a) may comprise a cubic gate system (2a.1) that slides through the joint (2a.2) until it joins the base (2a.3). This allows the cover to decrease in length as the retractable mechanism (2c) contracts.

In a preferred embodiment, the transmission cables (3b) are located in the posterior region of the cannula and follow the path in parallel; said cables (3b) have the function of sending the signals acquired by the sensors (3a) to a data collection system.

In another preferred embodiment, the sensors of the electronic sensing system may include, as an example and without the intention of limiting, mechanical sensors, such as optical limit switches, such as photoresistors and infrared and/or electromechanical ones, such as piezoelectric sensors.

In a preferred embodiment of the invention, the retractable element (2c) of the mechanical system can be used as a sensor of the electronic sensing system (3).

In a preferred embodiment of the invention, the wireless transmission of data from the controller to the device occurs via Bluetooth, WiFi, LiFi, NFC, among others.

BRIEF DESCRIPTION OF THE FIGURES

In order that the present invention may be easily understood and put into practice, reference will be made to the accompanying figures and the detailed description of one or more embodiments of the invention.

With reference to the attached figures.

DETAILED DESCRIPTION OF THE EMBODIMENT (S) OF THE INVENTION

Figure 1:
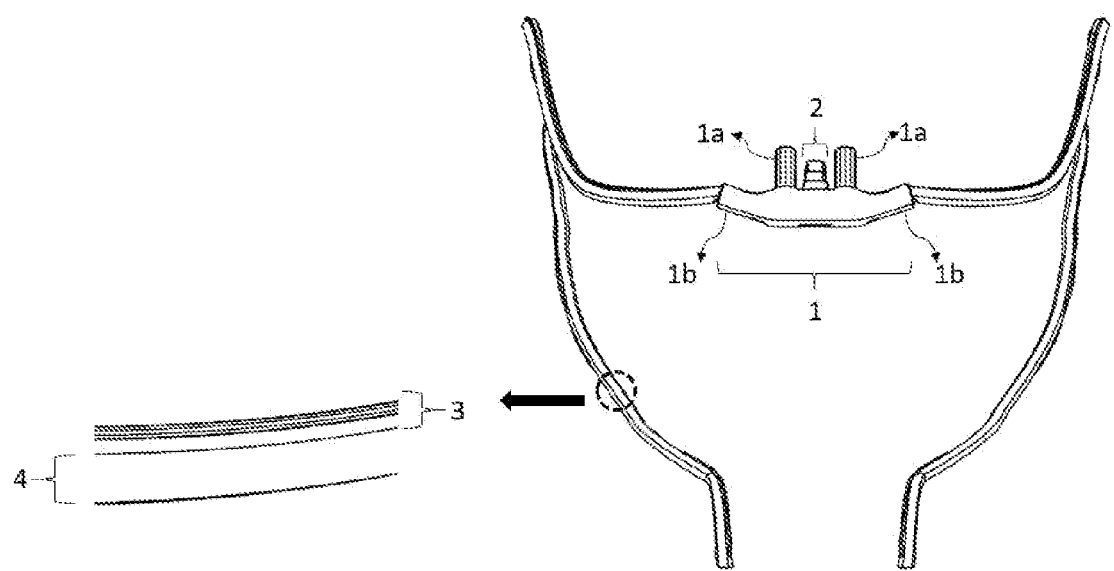
FIG. 1 shows the front view of the cannula of the present invention.

FIG. 1 shows the front view of the cannula of the present invention. In it, it is possible to see that the cannula comprises two openings (1a) that allow the passage of medicinal oxygen to the patient's nostrils and two openings (1b) that are connected with hoses (4) that are directed towards the oxygen source.

From FIG. 1 it is possible to identify that the mechanical system (2) of the invention is located in the middle of the two openings (1a) in order to come into contact with the patient's columella. In the same way, it is possible to show that the cables of the sensing system (3) are located right next to the hose (4) that connects the cannula to the oxygen source.

Figure 2:
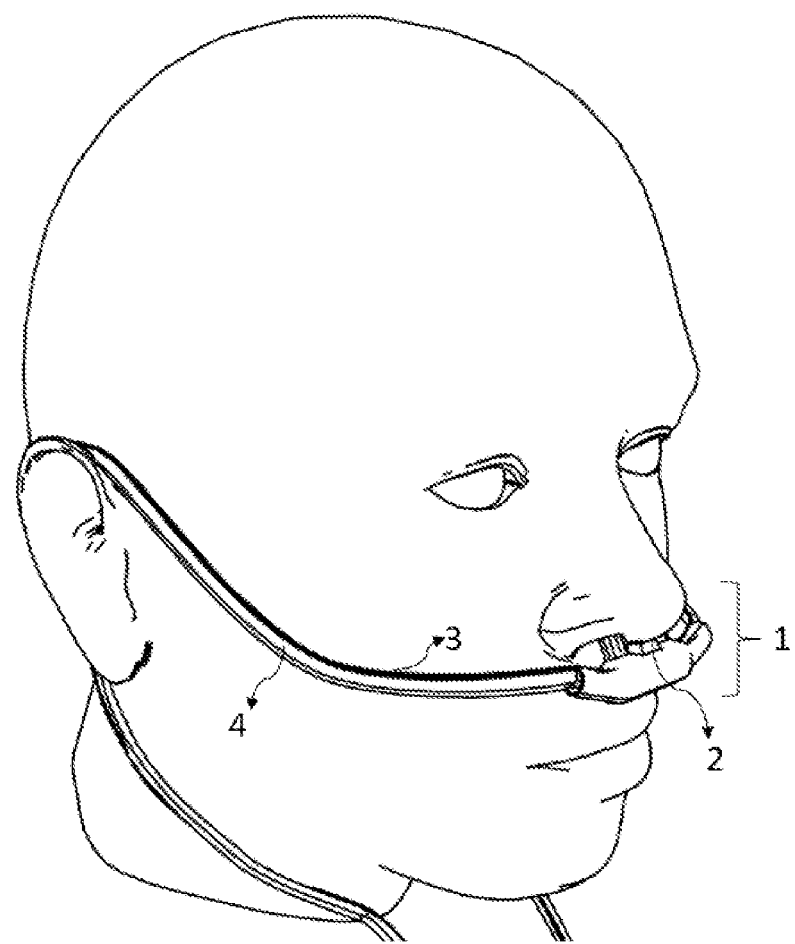
FIG. 2 represents a graphic illustration of the front-side view of the cannula of the invention placed on a user.

FIG. 2 discloses the frontal-lateral view of the cannula arranged on a user. When the user makes use of the present invention, the openings (1a) come into contact with the patient's nostrils and an element of the mechanical system comes into contact with the patient's columella, contracting the retractable element and allowing the passage of oxygen to the patient.

As an example, and without the intention of limiting the invention, the cables of the sensing system (3) and/or the hose (4) that connects the cannula to the oxygen source can be arranged behind the patient's ears as shown FIG. 2.

Figure 3:
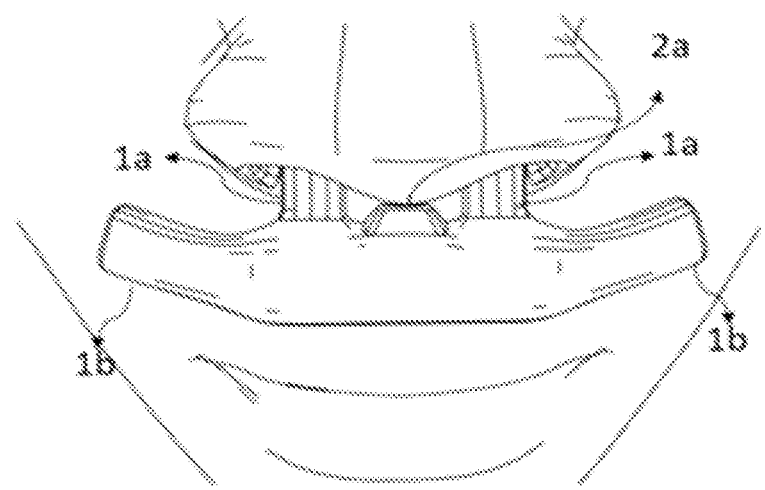
FIG. 3 represents a graphic illustration of the cannula when not connected to the user.
Figure 4:
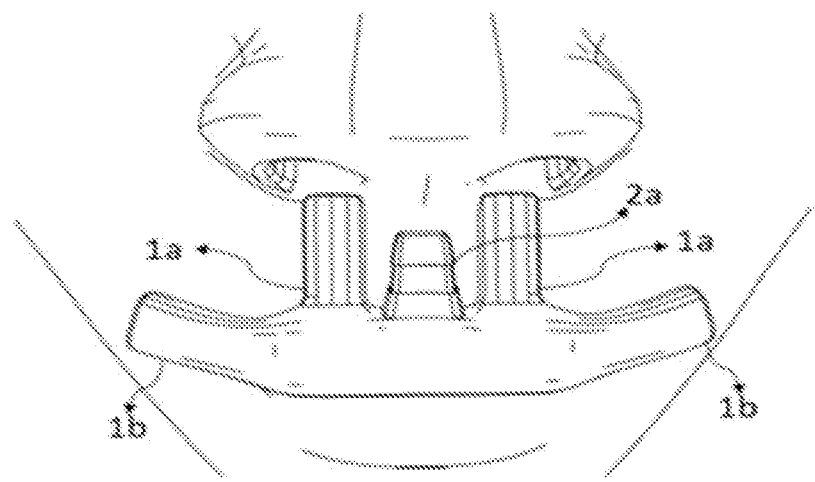
FIG. 4 represents a graphic illustration of the cannula of the invention coupled to the nostrils of the user.

FIGS. 3 and 4 show the general configuration of the cannula when coupled and uncoupled from the patient's nostrils, respectively. Thus, it is possible to show that when the cannula comes into contact with the patient's columella, the mechanical system (2), specifically the outer covering (2a), contracts in order to allow a change in the internal configuration that allows passage of oxygen from its source to the patient (FIG. 3).

On the contrary, if the cannula is not used or is misadjusted, the mechanical system will not come into contact with the patient's columella and, therefore, there will be no contraction of the outer covering that causes the passage of oxygen through the openings (1a) towards the patient (FIG. 4).

Figure 5:
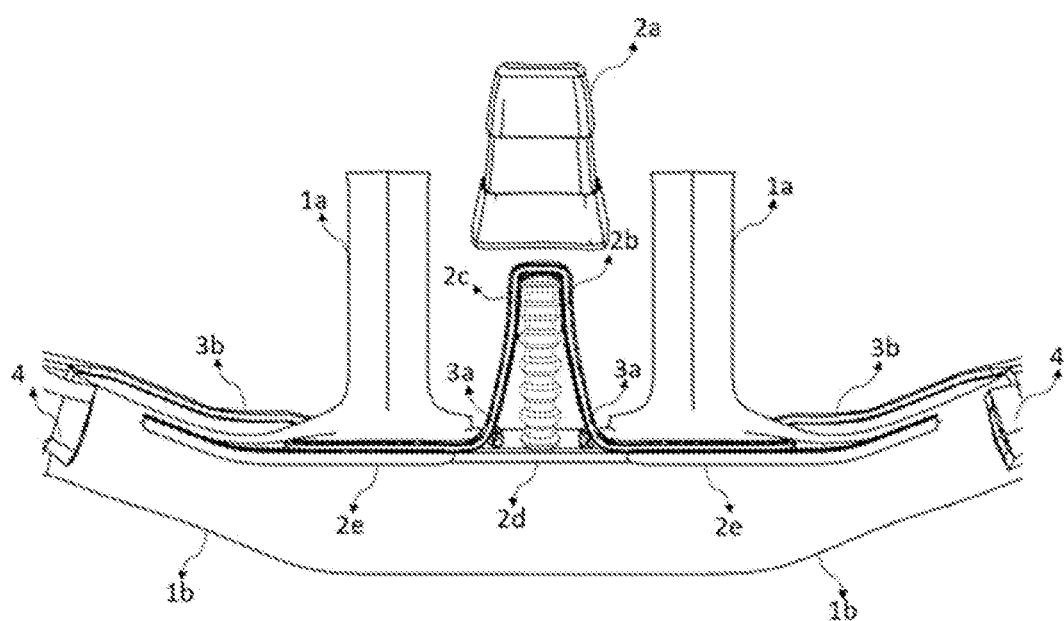
FIG. 5 shows a graphic illustration of the internal configuration of the mechanical system and the electronic component of the cannula.

FIG. 5 shows a graphic illustration of the internal configuration of the mechanical system and the electronic component of the cannula. From FIG. 5 it is possible to understand the operation of the cannula and its structural advantages with respect to others described in the state of the art.

As shown in the image, the mechanical system consists of a folded sliding gate (2b) that is attached to a retractable element (2c), such as a spring, positioned on a base (2d) that engages with the displacement directing elements (2e) arranged in the direction of the two openings (1b). Thus, when the retractable element (2c) contracts, due to the contact between the outer covering (2a) and the patient's columella, the gate (2b) is displaced and deployed through the displacement directing elements (2e). After said deployment, the holes of the gate (2b) are located parallel to the openings (1a) generating a pressure gradient that allows the circulation of oxygen towards the patient's nostrils.

On the other hand, the electronic sensing system (3) is arranged on the base (2d) and comprises sensors (3a) that detect the deployment of the gate (2b) and send an electronic signal through transmission cables (3b), arranged in the posterior region of the cannula, to a data collection system.

Figure 6:
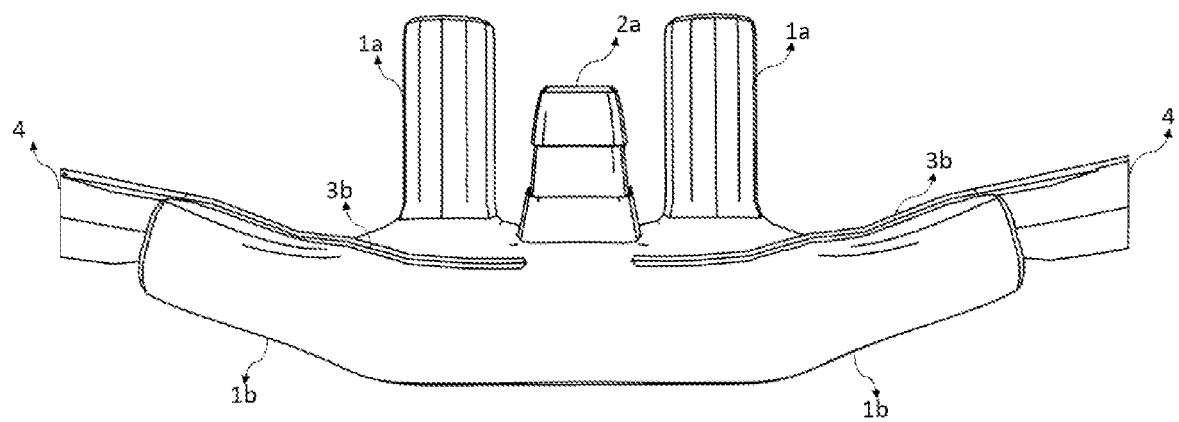
FIG. 6 shows a graphic illustration of the external configuration of the mechanical system and the electronic component of the cannula.

FIG. 6 shows a graphic illustration of the external configuration of the mechanical system and the electronic component of the cannula. Thus, it is possible to show that the mechanical system is covered by the outer covering (2a) and arranged between the two openings (1a) that allow the passage of medicinal oxygen to the patient's nostrils. The transmission cables (3b) of the electronic component (3) are arranged in the posterior region of the cannula together with the hoses (4) that are connected to the oxygen source.

Figure 7A:
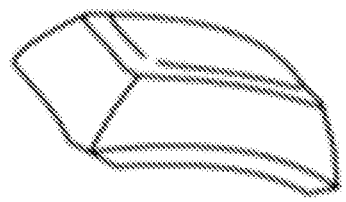
FIG. 7a is a graphic representation of the outer covering (2a) when it is not actuated.
Figure 7B:
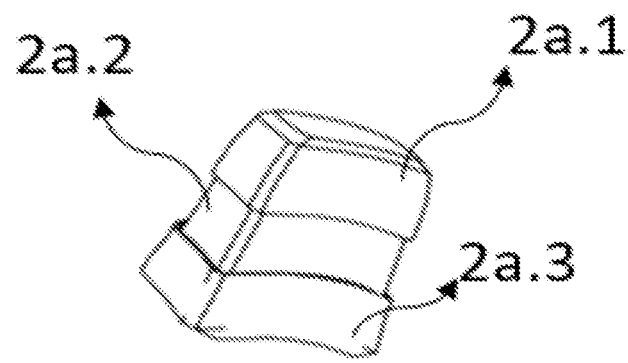
FIG. 7b is a graphic representation of the outer covering (2a) when actuated.

FIGS. 7a and 7b show a possible configuration of the outer covering (2a) when it is actuated and not actuated, respectively. In the case of FIG. 7a, it is possible to show that the outer covering (2a) is compressed by its contact with the patient's columella. On the contrary, in FIG. 7b the outer covering (2a) is observed without any contraction. In this case, it is possible to identify the elements that allow the operation of the outer covering (2a): a cubic gate system (2a.1) that can slide through a joint (2a.2) until it reaches a base (2a.3) fixed on the top face of the cannula.

Figure 8:
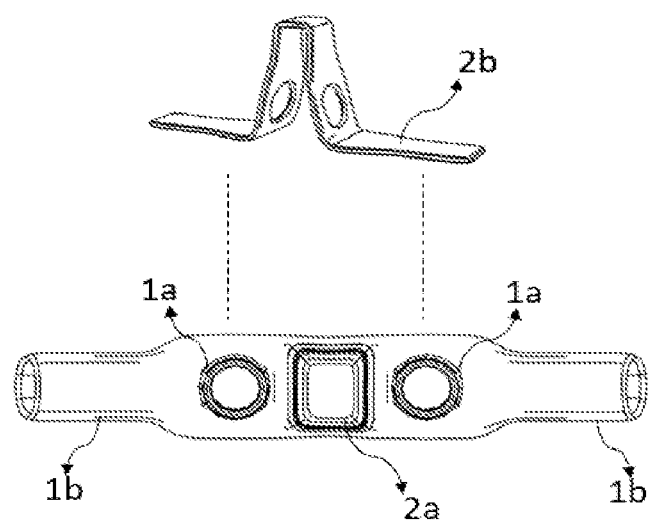
FIG. 8 discloses a graphical representation in top view of the relationship between the cannula and the sliding folded gate (2b) when it is folded.

FIG. 8 discloses a graphical representation in top view of the relationship between the cannula and the sliding folded gate (2b) when it is folded. In said image it is possible to observe that the circular openings (1a) that are directed towards the nostrils are obstructed by the ends of the sliding folded gate (2b). The above causes oxygen to not be delivered to the patient, thus avoiding medication waste.

Figure 9:
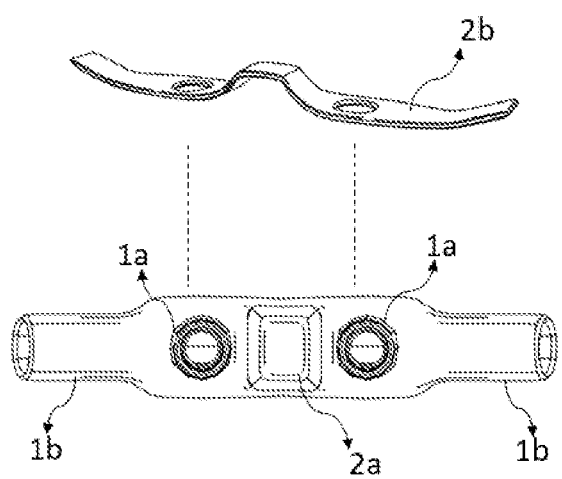
FIG. 9 discloses a graphical representation in top view of the relationship between the cannula and the sliding folded gate (2b) when it is deployed.

On the contrary, FIG. 9 shows a graphical representation in top view of the relationship between the cannula and the sliding folded gate (2b) when it is deployed. In this case, it is possible to appreciate that the circular openings (1a) that are directed towards the nostrils are free of obstacles, which allows the flow of oxygen to the patient.

Figure 10:
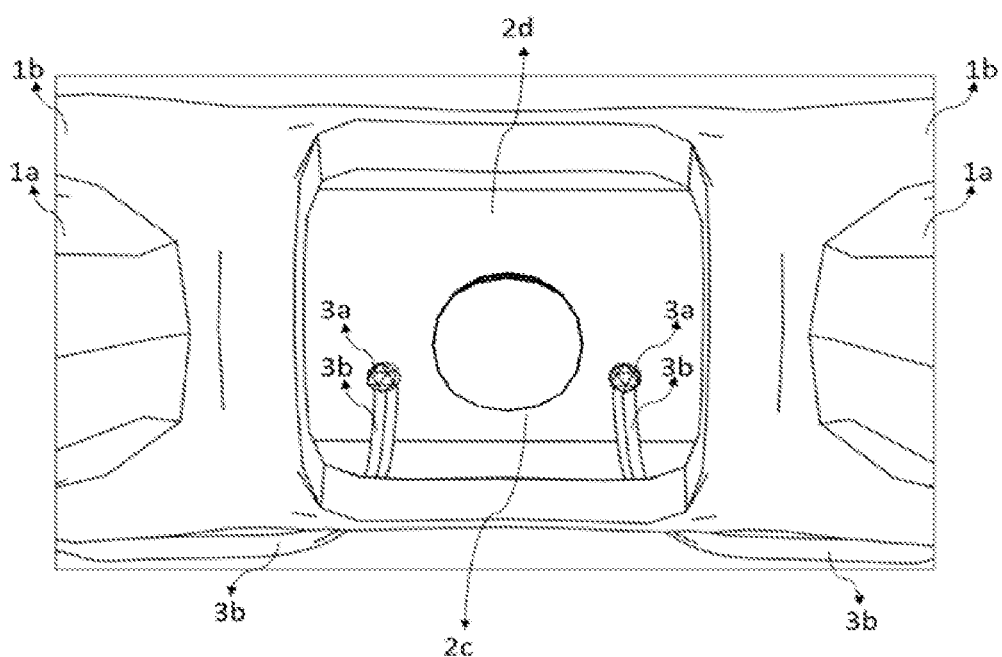
FIG. 10 shows a top view of the retractable element that acts as an activation mechanism and its relationship with the electronic component of the invention.

Finally, FIG. 10 shows a top view of the retractable element (2c) that acts as an activation mechanism and its relationship with the electronic component of the invention. From the figure it is evident that the electronic sensing system is positioned on the base (2d) in the same way as the retractable element (2c). The sensors (3a) are capable of detecting the deployment of the gate (2b), caused by the contraction of the retractable element (2c) and sending the electronic signal through transmission cables (3b) to a data collection system.

During specification, the embodiments of the invention that have been described do not limit the invention to any one embodiment or a collection of specific features. It is appreciated by those skilled in the relevant field of technology that, considering this disclosure, various modifications and changes can be made to particular exemplified embodiments without departing from the scope and intent of the present invention.

The following is claimed:

1. A nasal oxygen cannula that controls the supply of medical oxygen, wherein said cannula is characterized by comprising:
   a. a plastic tube with two openings (1a) directed to the user's nostrils and two openings (1b) that connect to hoses (4) coupled to an oxygen source,
   b. a mechanical system (2) arranged between the two openings (1a) directed to the nostrils (1a), where said system (2) consists of a sliding folded gate (2b) joined to a retractable element (2c) installed on a base (2d) connected with displacement directing elements (2e) arranged in the direction of the two openings (1b) that connect to the hoses (4),
   c. an outer covering (2a) that covers the mechanical system (2) and is fixed to the plastic tube (1a), and
   d. an electronic sensing system (3) arranged on the base (2d) comprising sensors (3a) that detect the deployment of the gate (2b) and send an electronic signal through transmission cables (3b), arranged in the back region of the cannula, to a data collection system.

2. The cannula of claim 1, characterized in that the retractable element (2c) of the mechanical system is a spring.

3. The cannula of claim 1, characterized in that the displacement directing elements (2e) include rails or channels.

4. The cannula of claim 1, characterized in that the number of displacement directing elements (2e) is an even number.

5. The cannula of claim 4, characterized in that the number of displacement directing elements (2e) is 4.

6. The cannula of claim 1, characterized in that the outer covering (2a) comprises a cubic gate system (2a.1), a joint (2a.2) through which the cubic gate system (2a.1) slides and a base (2a.3) to achieve contraction.

7. The cannula of claim 1, characterized in that the retractable element (2c) of the mechanical system is used as a sensor of the electronic sensing system (3).

8. The cannula of claim 1, wherein the data collection system consists of an analog-digital component that includes a feeding system for the sensors (3a), a processing system that acquires the analog data registered by the sensors (3a) and performs processing tasks such as counting the time of use, and a wireless data transmission system to a receiving device.

* * * * *